United States Patent [19]

Harootunian

[11] Patent Number: 5,589,351
[45] Date of Patent: Dec. 31, 1996

[54] FLUORESCENCE DETECTION APPARATUS

[75] Inventor: Alec T. Harootunian, Salt Lake City, Utah

[73] Assignee: NPS Pharmaceuticals, Inc., Salt Lake City, Utah

[21] Appl. No.: 350,232

[22] Filed: Dec. 6, 1994

[51] Int. Cl.$^6$ ............................................. C12Q 1/02
[52] U.S. Cl. ................................. 435/29; 422/63
[58] Field of Search ...................... 435/29, 291, 808; 422/52, 63; 250/328, 461.2; 356/246, 317–320, 417

[56] References Cited

U.S. PATENT DOCUMENTS

| | | | |
|---|---|---|---|
| 3,538,312 | 11/1970 | Genähar | 235/92 |
| 4,492,427 | 1/1985 | Lewis et al. | 350/96.2 |
| 4,594,533 | 6/1986 | Snook et al. | 315/363 |
| 4,626,684 | 12/1986 | Landa | 250/328 |
| 4,942,303 | 7/1990 | Kolber | 250/458.1 |
| 4,989,932 | 2/1991 | Landa | 350/96.1 |
| 5,053,626 | 10/1991 | Tillotson | 250/458.1 |
| 5,109,459 | 4/1992 | Eibert et al. | 385/115 |
| 5,112,134 | 5/1992 | Chow | 356/427 |
| 5,202,091 | 4/1993 | Lisenbee | 422/52 |

FOREIGN PATENT DOCUMENTS

| | | |
|---|---|---|
| 93/13423 | 7/1993 | WIPO . |
| WO93/13423 | 7/1993 | WIPO . |

OTHER PUBLICATIONS

Swatland H. J., Autofluorescence of Adipose Tissue . . . Meat Science 19 (1987) 277–284.
"The Use of Neuronal Human Receptors and Ion Channels as Targets for Innovative Drug Discovery", Kenneth A. Stauderman, Ph.D., High Throughput Screening for Drug Discovery, Aug. 10–11, 1994, San Francisco, California.
"Fluorescence Imaging Creates a Window on the Cell", Roger Y. Tsien, Chemical and Engineering, Jul. 18, 1994, pp. 34–44.
"Fluorescent Indicators for Cytosolic Calcium Based on Rhodamine and Fluorescein Chromophores", Akwasi Minta et al., The Journal of Biological Chemistry, vol. 264, No. 14, May 15, 1989, pp. 8171–8178.
"Fluorescence Measurement and Photochemical Manipulationof Cytosolic Free Calcium", Roger y. tsien Tins, vol. 11, No. 10, 1988, pp. 419–424.
"Fluorescent Probes of Cell Signaling", Roger y. Tsien, 1989, 12; pp. 1227–1253
"Series 7600 Microplate Fluorometers" product information sheet, Cambridge Technology, Inc.
"FLIPR—the next generation fluorescent plate reader" product information sheet; NovelTech Systems, Inc.
"The CytoFluor™ 2300 Fuorescence Measurement System" product information sheet, Millipore.

Primary Examiner—Ralph J. Gitomer
Attorney, Agent, or Firm—Madson & Metcalf

[57] ABSTRACT

A fluorescence analysis system detects light transmitted from wells in a sample plate. One embodiment of the system includes a single light detector. A reflector is capable of receiving light from any one of several detection emitters and of reflecting the light toward the light detector. One reflector includes a prism which is mounted on a stepping motor. The prism is selectively rotated so that it faces each detection emitter in turn. The light from several wells in a row is directed toward the light emitter by rotating the prism to face, one-by-one, each of the emitters corresponding to the wells. The detection emitters include one end of an optical fiber bundle. The other end of each bundle is positioned near the wells, with each bundle positioned by a different well to carry light from that well to the corresponding emitter. A collimating lens is positioned between each detection emitter and the rotating prism to focus light from the emitter onto the prism. A baffle is positioned between the light detector and the prism. Light from a xenon arc excitation lamp is carried by optical fiber bundles toward the sample wells. A computerized controller coordinates light detection with the activities of an automated liquid handling system.

21 Claims, 7 Drawing Sheets

FLUORESCENCE DETECTION APPARATUS

FIELD OF THE INVENTION

The present invention relates to a system for detecting light emitted from compositions held in a plurality of sample wells, and more particularly to a system which detects fluorescence in compositions during automated testing by carrying light from a plurality of sample wells to a single light detector such as a photomultiplier tube. The invention is further related to a method for screening drugs and similar compositions for their effects on various cell receptors and channels, particularly calcium receptors and channels.

TECHNICAL BACKGROUND OF THE INVENTION

A wide variety of scientific tests and procedures involve the analysis of photochemical reactions generally and the analysis of fluorescence in particular. Fluorescence is analyzed in research settings to identify and study both organic and inorganic compounds. Fluorescence is analyzed in clinical settings to obtain measurements in connection with immunoserology, microbiology, toxicology, clinical chemistry, histopathology, and coagulation assessment. In the industrial and agricultural arenas, fluorescence analysis is used during toxicity assays and contamination studies. Fluorescence is also analyzed in many contexts to study enzymes, amino acids, carcinogens, and a wide variety of other chemical compounds.

Fluorescence analysis also finds useful application in drug screening tests. The development of safe and effective drugs typically involves an extremely large number of tests. Fortunately, some of the required tests may be partially automated. For instance, tests to screen out ineffective compositions are often performed in large part by automatic machinery. Automation increases the number of compositions that can be tested, and also reduces the risk of error that often comes with repetitive tasks.

Automated screening tests typically begin by placing cell samples in several sample wells. The sample wells are small, cylindrical receptacles formed in a rectangular array in a transparent plastic sample plate. The typical sample plate contains an eight by twelve array of wells. Although the terms "row" and "column" are often used to designate a line of wells in the array, usage of these terms varies, with some sources referring to eight rows and twelve columns and others referring to eight columns and twelve rows. Without limiting the number of wells in a row, the latter usage is adopted herein. Thus, a typical row contains eight wells, but a row may also contain some other number of wells.

The cell samples are placed in the wells one well at a time or one row at a time by an automated liquid handler. A typical automated liquid handler includes a controller, at least one positionable row of pipettes, a subsystem for positioning the pipettes, and a subsystem for selectively directing a measured quantity of fluid through the pipettes. Some liquid handlers also include a subsystem for positioning a sample plate. The controller typically includes a programmed computer.

The pipettes are spaced apart from one another by the center-to-center distance between the sample wells in a standard sample plate. Thus, each pipette will fit in a separate sample well if the row of pipettes is placed over the row of wells and then lowered. At a minimum, the pipettes may be raised and lowered; many liquid handlers also permit the pipettes to be positioned in other ways.

In operation, cell samples to be studied are placed in the wells. The cell samples contain cells or cell contents which the unknown drug or other reagent being tested will act upon. The pipettes are positioned within a row of wells, and a first composition is injected into the cell samples through the pipettes. The composition, which is selected according to the test protocol, may include drugs or agonists. The pipettes are then positioned within the next row, and the process is repeated until the plate is filled.

Base line measurements are taken to calibrate the system. Thus, in the case of reactions which emit light, the level of light coming from each well is measured to determine the base line. All light emitted from the sample well may be monitored, or the light may be filtered before it is measured. For example, some drug screening tests involve the measurement of fluorescent light having a predetermined wavelength.

If the test protocol so requires, additional compositions may be added. The pipettes are rinsed, and then the second composition is added to the cell samples and the first composition so that additional reactions may be measured. Addition of the second composition is accomplished by positioning the pipettes in the wells that already contain the first composition and directing the second composition through the pipettes. The light coming from each well is again measured to gain experimental data. After rinsing, further compositions may be added and assessed in similar fashion.

In certain screening tests, the effectiveness of various compositions is measured by detecting and measuring the amount of light emitted from the sample well as the materials and cells in the sample wells react. In other screening tests, the amount of light transmitted through the well from a source external to the well is a useful measure of the desirability of particular compositions. Thus, instruments are needed which detect and measure at least a portion of the light from each sample well.

A conventional approach to detecting and measuring light involves directing a portion of the light emitted from each well in a row to a corresponding light detector in a row of light detectors. For instance, one system uses a row of fiber optic cables to carry light from a row of wells to a row of photomultiplier tubes. Each cable carries light from one well to one photomultiplier tube.

Such systems permit the light from an entire row of wells to be detected and measured at the same time, because the light from each well is directed to a different light detector. Processing an entire row at one time increases the number of wells that can be processed, which in turn reduces the time required to perform fluorescence analysis.

A problem in the art is that photomultipliers and other light detectors are typically expensive. Moreover, each light detector normally requires supporting equipment in order to detect and measure light. The necessary supporting equipment, which typically includes a power supply and a set of control electronics equipment, is often expensive and bulky. Thus, the use of a full row of light detectors adds substantially to the cost, size, and complexity of the light detection systems used in fluorescence analysis.

Another conventional system carries light from an entire plate of wells to a cooled charge-coupled device (CCD) camera. A CCD camera includes a rectangular array of picture elements known as pixels. The output of the entire sample plate is imaged on the CCD. Particular pixels corresponding to each well are then sampled to obtain light intensity readings for each well. Multiple wells in a row, or multiple rows of wells, can thus be processed in parallel and the time required for testing can be reduced.

Cooled CCD cameras are also extremely expensive in comparison to other types of light detectors. In addition, strong light sources, such as 1000 watt lights, are needed to illuminate the entire plate at once. Use of such strong lights is expensive, both because the lights themselves are costly, and because special optical elements must be used in connection with the strong light source. Moreover, costly secondary image processing is typically used to sample the pixels and to extract appropriate data from the CCD output.

Calcium is probably the most important and ubiquitous messenger linking plasma membrane depolarization to activation of intracellular biochemical events such as transmitter secretion or enzyme activation. Intracellular calcium ion ($Ca^{+2}$) also plays a key role in mediating the actions of many transmitters, hormones, and drugs that act on plasma membrane receptors. At the heart of both voltage and receptor triggered calcium ion signalling is the intracellular or cytosolic free calcium ion concentration.

In order to measure calcium ion flow and change, molecular probes have been synthesized which can be placed within the cells to detect and reversibly bind messenger molecules and act as imaging agents. Fluorescence probes are the most popular because fluorescence is usually highly specific, extremely sensitive, and amenable to microscope detection.

Many clinically valuable drugs act by modulating calcium ion or calcium regulated enzymes. Channel blockers such as verapamil and nifedipine are used to treat angina and inhibit the entry of calcium into the heart or arterial smooth muscle cells by blocking calcium conducting channels.

One example of the importance of calcium ion flow is illustrated by the function of the regulatory parathyroid hormone (PTH). As mentioned above, intracellular calcium ion plays a pivotal role in regulating vaious cellular responses. The same is true with respect to extracellular calcium function, which is known to control various life-sustaining processes such as blood clotting, nerve and muscle excitability, and proper bone formation. PTH is known to act on kidney and bone tissue to increase the level of $Ca^{+2}$ in the blood. Elevated levels of plasma $Ca^{+2}$ in turn act in a negative feedback capacity to depress secretion of PTH.

The discovery of the $Ca^{+2}$ receptor indicates the manner in which $Ca^{+2}$ acts not only intracellularly to regulate various cellular functions but also extracellularly to regulate the activity of certain cells in the body. In both cases, $Ca^{+2}$ interacts with a receptor protein. Those receptors within the cell are high-affinity $Ca^{+2}$ binding proteins and are essentially ubiquitous. Those receptors on the cell surface are low affinity $Ca^{+2}$ binding proteins and are restricted in their expression to certain specialized cells, many of which are intimately involved in bodily $Ca^{+2}$ homeostasis.

Thus, it would be an advancement in the art to provide a system for detecting light during fluorescence analysis without using a separate light detector for each sample well in a typical row of sample wells. It would also be an advancement in the art to provide such a system which effectively detects fluorescent light in a predetermined range of wavelengths. It would be a further advancement to provide such a system which can be used effectively in combination with an automated liquid handler.

It would also be an advancement to provide an efficient and effective screening technique for determining the effect that various drugs or other reagents have on calcium function. It would be a related advancement to provide effective screening methods to determine whether a particular drug or reagent was a calcimimetic or calcilytic material, as those terms are defined herein.

Such a system is disclosed and claimed herein.

BRIEF SUMMARY OF THE INVENTION

In one aspect, the present invention provides a system for detecting light transmitted from one or more sample wells of a sample plate during fluorescence analysis, or during other types of analysis that are based upon changes in light emitted or reflected from a sample. The sample plate has several wells per row, and may contain one or more rows. During analysis, light may be emitted from compositions in the well as part of a chemical reaction. The mechanics of this type of reaction involving calcium will be discussed in additional detail below. Light may also be transmitted through the well from a source external to the well. In either case, the present system detects the light and provides data that may be used to screen out ineffective compositions and otherwise assist in analysis of chemical changes in each sample well.

The detection system preferably includes a single light detector, but in any case will typically include fewer light detectors than the number of wells in a typical sample plate row. Using the present system it is not necessary to dedicate one light detector to each well in a row. Instead, the system switches the input from a plurality of wells to a single light detector over time.

The light detector includes a photomultiplier tube. Thus, the light-switching capability of the present invention substantially reduces the cost and complexity of the light detectors and light detector supporting equipment required to effectively detect light from a row of sample wells.

The system also includes a reflector which is capable of selectively receiving light from any one of a plurality of detection emitters and of reflecting the light toward the light detector. In one embodiment, the reflector includes a prism which is mounted for rotation about a central axis. The prism is secured to the shaft of a stepping motor, and an optical encoder is positioned adjacent the stepping motor.

In one embodiment, the detection emitters are stationed around the prism in an emitter plane that is perpendicular to the central axis. The light detector is positioned above the emitter plane on the central axis. Using the optical encoder and the stepping motor to monitor and change the position of the prism, the prism is selectively rotated so that it faces each detection emitter in turn.

Selectively rotating the prism to face one of the emitters permits the light from the selected emitter to be reflected by the prism out of the emitter plane and along the central axis to the light detector. The sides and back of the prism are masked by light barriers, so that no light is reflected to the light detector from emitters which are not selected. The light from several wells in a row, or from all the wells, is directed toward the light emitter by rotating the prism to face, one-by-one, each of the emitters corresponding to the wells.

In an alternative embodiment, the reflector includes a removed cone prism fixed in position about a central axis. The detection emitters are again stationed in a circle in a plane perpendicular to the central axis, and the light detector is again positioned above the emitter plane on the central axis. A shutter separates each emitter from the removed cone prism. Selectively opening a particular shutter permits the light from the corresponding emitter to be reflected by the prism out of the emitter plane and along the central axis to the light detector.

In a further embodiment, the reflector may include a fiber optic bundle for each emitter. One end of each bundle is separated from the emitter by a shutter, and the other end of each bundle is positioned near the light detector. Thus, selectively opening one shutter permits the light from the corresponding emitter to be carried by the corresponding bundle to the light detector.

In each of these embodiments, the detection emitters include one end of an optical fiber bundle. The other end of each bundle is positioned near the wells, with each bundle positioned near a different well to carry light from that well to the corresponding emitter. The fiber bundles thus form a plurality of detection carriers, each of which is capable of carrying light from one of the wells to one of the detection emitters.

A collimating lens is positioned between each detection emitter and the reflector in the rotating prism and fixed prism embodiments. Each lens collimates the light from the emitter and directs that light onto the prism. To reduce the impact of ambient or stray light may which reach the light detector, a baffle may be positioned between the light detector, on the one hand, and the prism or the converging bundle ends, on the other.

Some embodiments of the present invention also include a subsystem for directing an excitation light toward the wells. One embodiment includes an excitation light source in the form of a xenon arc lamp with a collimation lens. Several excitation carriers made with optical fiber bundles carry light from the excitation light source toward selected sample wells. The excitation fibers and the detection fibers are interleaved near the sample wells to obtain more uniform excitation and detection.

A computerized controller coordinates light detection with liquid handling by communicating with an automated liquid handling system. Status and control information directed between the light detection system and the liquid handler permit effective coordination of light detection, light excitation, liquid handling, and sample well positioning.

Thus, the present invention provides a system for detecting light during fluorescence analysis without using a separate light detector for each sample well in a typical row of sample wells. Instead, the light from each well is carried in turn to the reflector, which reflects the light into the light detector. Unlike conventional approaches, it is not necessary to dedicate one light detector to each well in the row. The present invention also provides a system which effectively detects fluorescent light of a particular wavelength. Filters and a baffle are employed to remove light outside the desired wavelength range. Moreover, the present system is readily coordinated with an automated liquid handler.

One use of the apparatus of the present invention is in screening various drugs and other chemical or biological reagents for their effects on intracellular and intercellular calcium ion flow. It will be appreciated that a wide range of drugs and chemical agents may be the subject of testing. However, for purposes of ease of discussion, such agents as a group will be referred to herein as "drugs."

In order to screen for such effects, cells in the sample wells are labelled with fluorescent calcium indicators. Traditional fluorometric indicators of calcium ion had significant limitations that prevented the effective screening of drugs for their effects on cellular calcium ion flow using an apparatus of the type described herein. For example, some conventional indicators could not distinguish between $Ca^{+2}$ and $Mg^{+2}$. Other indicators required high pH that damaged cells.

Recently, however, a new group of fluorescent indicators have been developed which indicate the presence of $Ca^{+2}$ and have visible excitation and emission wavelengths. Five representative compounds of this nature have been designated rhod-1, rhod-2, fluo-1, fluo-2, and fluo-3. Generally, these compounds combine the 8-coordinate tetracarboxylate chelating site of 1,2-bis(2-amino-phenoxyethane-N,N,N',N'-tetraccetic acid with a xanthane chromophore to give a rhodamine-like or fluorescine-like fluorophore. Materials of this type have been described in the literature and are readily available. See, for example, Minta, et al, "Fluorescent Indicators for Cytosolic Calcium Based on Rhodamine and Fluorescein Chromophores," J. Biol. Chem. 264:8171–8178 (1989); Kao, et al, "Photochemically Generated Cytosolic Calcium Pulses and Their Detection by Fluo-3," J. Biol. Chem. 264:8179–8184 (1989), both of which are incorporated herein by this reference.

A further problem in the existing art was the fact that many specialized fluorescence instruments required laser excitation which is more expensive to produce in the UV compared to the visible range. UV wavelengths are also potentially injurious to cells and tend to excite autofluorescence. All of these problems would be avoided by the use of indicators whose excitation wavelengths were in the visible or infrared ranges.

Using the designated indicators, binding of calcium ion increases fluorescence by up to 40 times. This is a very dramatic increase and is readily measurable using the apparatus of the present invention. It is important to note, however, that these indicators do not typically provide a wavelength shift, as did some known indicators. Accordingly, it is not possible to employ measurements using ratios of wavelengths. However, if UV excitation is used, or if other indicators are used which can be excited with visible light and have suitable wavelength shifts upon binding with calcium, ratios of wavelengths can be measured using the apparatus and methods of the present invention.

Thus, the present invention provides methods and apparatus for avoiding the problems encountered in the art. According to the methods of the present invention, the new effective fluorometric indicators, such as fluo-3, can be used. At the same time, the apparatus of the present invention provides means for rapidly reading fluorescence using visible light.

These and other features and advantages of the present invention will become more fully apparent through the following description and appended claims taken in conjunction with the accompanying drawings.

BRIEF DESCRIPTION OF THE DRAWINGS

In order to illustrate the manner in which the above-recited and other advantages and features of the invention are obtained, a more particular description of the invention summarized above will be rendered by reference to the appended drawings. Understanding that these drawings only provide selected embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
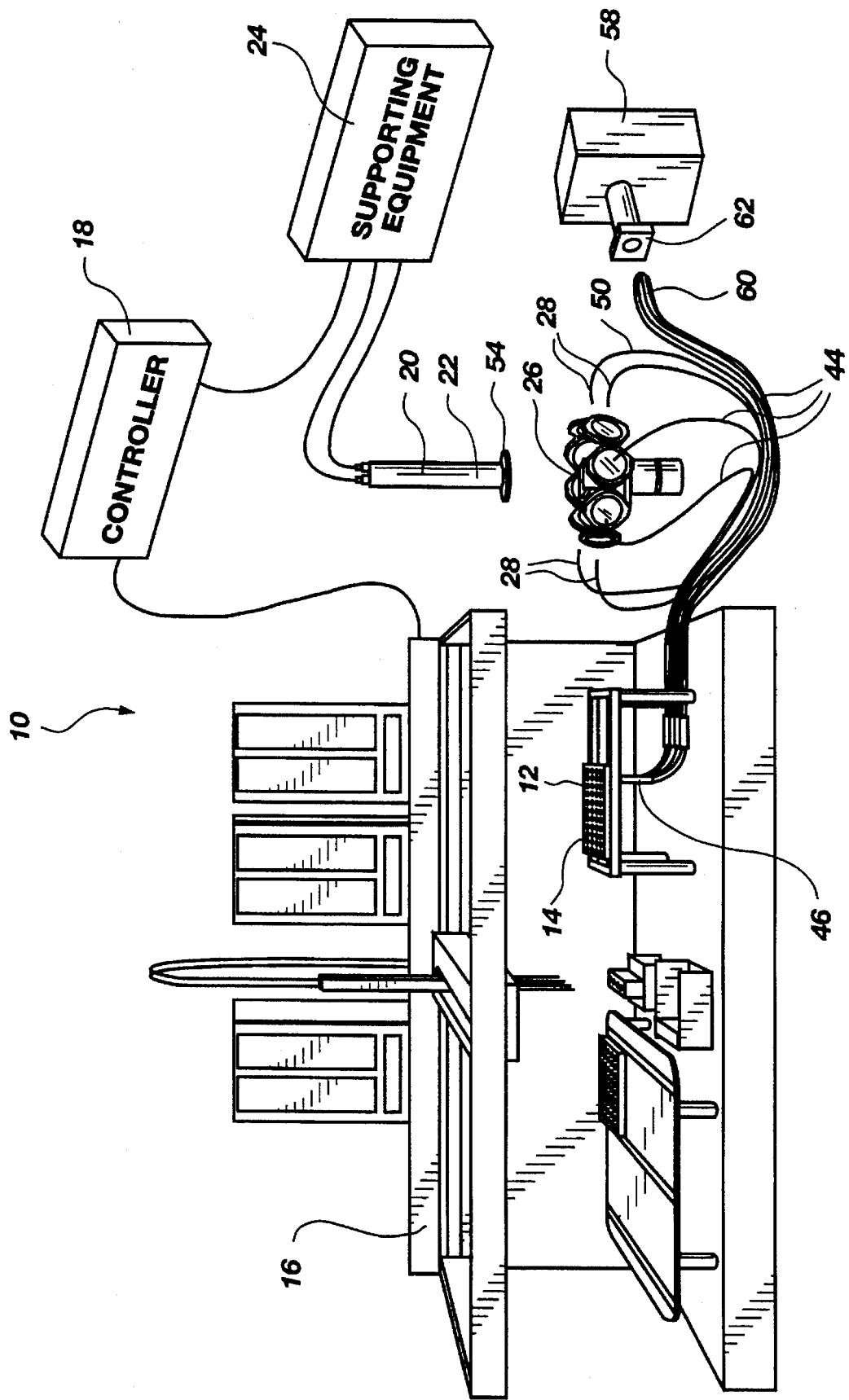
FIG. 1 illustrates one embodiment of a fluorescence detection system according to the present invention, with supports removed for clarity of illustration.

Reference is now made to the figures wherein like parts are referred to by like numerals. The present invention relates to a system, which is designated generally at 10 in FIG. 1, for detecting light transmitted from one or more sample wells 12. The sample wells 12 are arranged in rows in a sample plate 14. The sample plate 14 may have eight, a dozen, or another number of wells 12 per row, and the plate 14 may contain one or more rows. Each well 12 typically holds from about 0.05 cubic centimeters to about 0.30 cubic centimeters of fluid.

The sample plate 14 is disposed within an automated liquid handler 16. The automated liquid handler 16 is preferably equipped with digital I/O capabilities for communication and control. One suitable automated liquid handler with digital I/O is the Hamilton 2200 MPH option 2, 36552, available from Hamilton of Reno, Nev.

A controller 18 is in signal communication with the automated liquid handler 16. One suitable controller 18 includes two IBM-compatible personal computers, such as a model 386SX25 and a model 486DX66. The computers are equipped with software which coordinates the automated liquid handler 16 with other elements of the system 10 according to the teachings herein. The controller 18 also includes an analog-to-digital converter and digital I/O board for computer data acquisition. One suitable data acquisition board includes the model CYRDAS 8, available from Cyber Research of Branford, Conn.

In the embodiment illustrated, the detection system 10 includes a single light detector 20. Other embodiments of the present invention include a plurality of light detectors, but each embodiment includes fewer light detectors than the number of wells in one row of the sample plate used with that embodiment.

The light detector 20 includes a photomultiplier tube 22. One suitable photomultiplier tube 22 is the model 9124B in a housing model RFIQL30, available from Thorn EMI of Rockaway, N.J. Suitable photomultiplier supporting equipment 24, which is in communication with the photomultiplier tube 22 and the controller 18, includes a power supply and detection circuitry available from the Biomedical Instrumentation Group, University of Pennsylvania, in Philadelphia, Pa. Alternative embodiments of the light detector 20 include a photomultiplier cell, a CCD camera, a photodetector, a photodiode, or an avalanche photodiode in place of, or as a supplement to, the photomultiplier tube 22 "Certain embodiments may include a wavelength filter positioned between the photomultiplier tube and the prism, the wavelength filter allowing passage of light having a wavelength in the range from about 510 nanometers to about 550 nanometers."

The system 10 also includes a reflector 26 disposed within a plurality of detection emitters 28. As used herein, the term "reflector" includes prisms, mirrors, beam splitters, lenses, optical fiber bundles, and other optical elements which are capable of changing the direction of travel of a beam of light.

Figure 2:
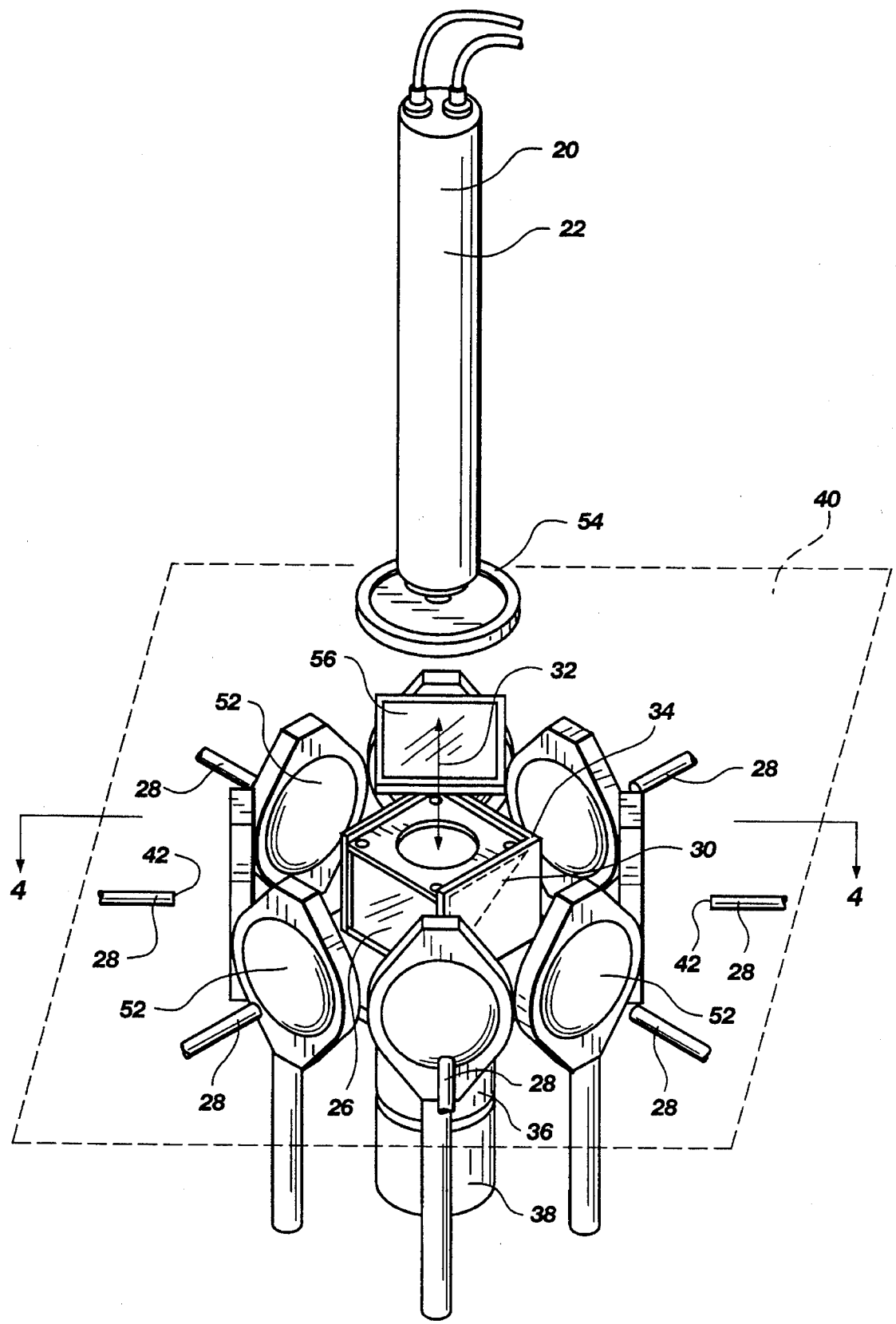
FIG. 2 further illustrates several detection emitters, lenses, filters, a reflector, and a light detector from the embodiment shown in FIG. 1.

With reference to FIGS. 1 and 2, the reflector 26 includes a prism 30 which is mounted for rotation about a central axis 32. One suitable prism 30 is the right-angle prism model 40.0070 available from Rolyn Optics of Covina, Calif. The sides and back of the prism 30 are masked by a light barrier 34. The barrier 34 is formed of paint, cardboard, metal, or another opaque material and is secured to the prism 30 by adhesive or other conventional means.

The prism 30 is secured to the shaft of a stepping motor 36 such that the prism 30 and the shaft rotate in unison. An optical encoder 38 is positioned adjacent the stepping motor 36 and is configured to produce a signal corresponding to the current rotational position of the stepping motor 36 about the central axis 32. One suitable microstepping motor and encoder combination is the model S57-51-E available from Parker Compumotor Division of Rohnert Park, Calif. A suitable controller for the microstepping motor 36 is the model SX available from Parker.

The detection emitters 28 are stationed in a circle in a plane 40 (shown in phantom in FIG. 2) perpendicular to the central axis 32. The light detector 20 is positioned above the emitter plane 40 on the central axis 32. Each detection emitter 28 includes one end 42 of an optical fiber bundle 44. To reduce cost and increase light gathering capability, each fiber bundle 44 preferably includes glass fibers. However, quartz fibers may also be employed. One suitable fiber bundle 44 is the model 77533 bifurcated fiber optic bundle available from Oriel Corporation of Stratford, Conn.

Figure 3:
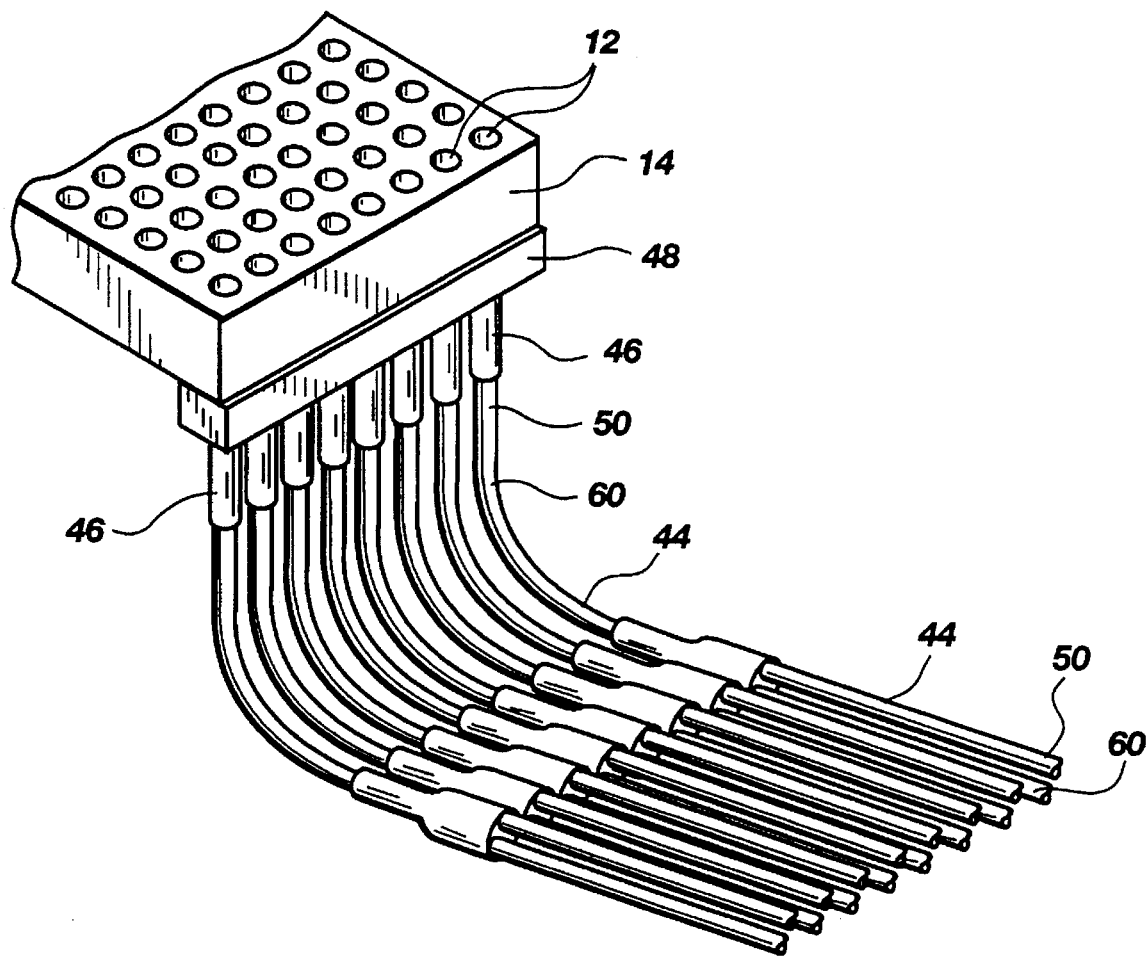
FIG. 3 further illustrates several detection carriers and excitation carriers from the embodiment shown in FIG. 1.

With reference to FIGS. 1 and 3, the opposite end 46 of each fiber bundle 44 is positioned near the sample wells 12. The bundle ends 46 are secured within a frame 48. Each of the bundle ends 46 is positioned near a different one of the wells 12, in order to carry light from that well 12 to the corresponding one of the emitters 28. Fibers within the fiber bundles 44 form a plurality of detection carriers 50, each of which is capable of carrying light from one of the wells 12 to one of the detection emitters 28.

With reference to FIG. 2, it is presently preferred that a lens 52 be positioned between each detection emitter 28 and the prism 30. Each lens 52 is preferably a collimating lens. One suitable lens 52 is the model 17.1175 collimation lens available from Rolyn Optics of Covina, Calif.

To reduce the impact of ambient or stray light on the light detector 20, a baffle 54 is preferably positioned between the light detector 20 and the prism 30. Suitable baffles include the model ID-1.5 iris diaphragm available from Newport Corporation of Irvine, Calif., and the model 71400 iris diaphragm available from Oriel Corporation of Stratford, Conn.

Some embodiments of the present invention, including the embodiment illustrated in FIG. 2, are directed to the detection of light having a particular wavelength. Accordingly, a filter 56 is employed to screen out light of undesired wavelengths. To detect fluorescent light having a wavelength in the range from about 510 nanometers to about 555 nanometers, the filter 56 includes a dichroic filter positioned between the rotating prism 30 and the photomultiplier tube 22. One suitable filter 56 includes two model 510DRLP dichroic mirrors available from Omega Optical of Brattleboro, Vt. The filter 56 includes an emission filter that is positioned between the dichroic filter and the photomultiplier 22. Suitable emission filters include the model 540DF25 filter available from Omega Optical of Brattleboro, Vt. and the model D535/40 filter available from Chroma Technology of Brattleboro, Vt.

Those of skill in the art will appreciate that filters may also be placed elsewhere along the optical path between a sample well 12 and the light detector 20. However, to reduce the number of filters needed, filters are preferably positioned along a common light path near the light detector 20 rather than along the light path for each detection emitter 28. A common light path is a path along which light from more than one of the wells 12 may travel.

With reference to FIGS. 1 and 3, the system 10 also includes a subsystem for directing an excitation light toward the wells 12. The excitation subsystem includes an excitation light source 58 in the form of an arc lamp. Suitable lamps include a xenon arc lamp with collimation lens and power supply, such as the 75 watt model 60064 available from Oriel Corporation of Stratford, Conn. and the 150 watt arc lamp available from Opti-Quip of Albany, New York which may include a model 1600 power supply and a model 770 U lamphouse "In certain embodiments of the present invention the light produced by the excitation light source will preferably have a wavelength in the range of form about 470 nanometers to about 500 nanometers".

The excitation subsystem also includes several excitation carriers 60. Each excitation carrier 60 includes a portion of one of the optical fiber bundles 44. Each excitation carrier 60 carries light from the excitation light source 58 toward one of the sample wells 12. Within the end of the fiber bundle 44 near the wells 12, excitation optical fibers of the excitation carrier 60 are preferably interleaved with detection optical fibers of the detection carrier 50 to obtain more uniform excitation and detection.

An excitation filter 62 is positioned between the excitation light source 58 and the excitation carriers 60. Suitable excitation filters 62 include the model 485DF22 filter available from Omega Optical of Brattleboro, Vt. and the model D480/30 filter available from Chroma Technology of Brattleboro, Vt.

With reference to FIGS. 1 and 2, the excitation light 58, the filters 56 and 62, the fiber optic bundles 44, and the light detector 20 are chosen to operate in the wavelengths that are of interest. For instance, assume that the system 10 is being employed during drug screening tests and that effective compositions fluoresce at a first wavelength, termed the "fluorescence emission wavelength," as part of a photochemical reaction. Assume also that a composition of interest is excited by light having a second wavelength, termed the "excitation wavelength."

Then the excitation light emitted by the excitation light source 58 should include a wavelength approximately equal to the excitation wavelength. The light detector 20 should be capable of detecting light having a wavelength approximately equal to the fluorescence emission wavelength. The detection filter 56 should screen out light whose wavelength is not approximately equal to the fluorescence emission wavelength. The detection carriers 50 and the excitation carriers 60 should be capable of transmitting light having wavelengths approximately equal to the fluorescence emission wavelength and the excitation wavelength, respectively. Finally, the material used to form the sample wells 12 should be capable of transmitting light having wavelengths approximately equal to the fluorescence emission wavelength or the excitation wavelength.

In operation, the present invention provides a system 10 for detecting light transmitted from one or more of the sample wells 12 during fluorescence analysis, and for exciting the contents of the wells 12 with light of a specified wavelength. Light emitted from a well 12 travels into the corresponding detection carrier 50. The optical fibers in the detection carrier 50 then carry the light to the corresponding emitter 28.

Light may be carried to several of the emitters 28 at the same time. However, the prism 30 is aligned with at most one emitter 28 at any given time. Light from emitters 28 with which the prism 30 is not currently aligned will not be reflected by the prism 30 toward the light detector 20.

Figure 4:
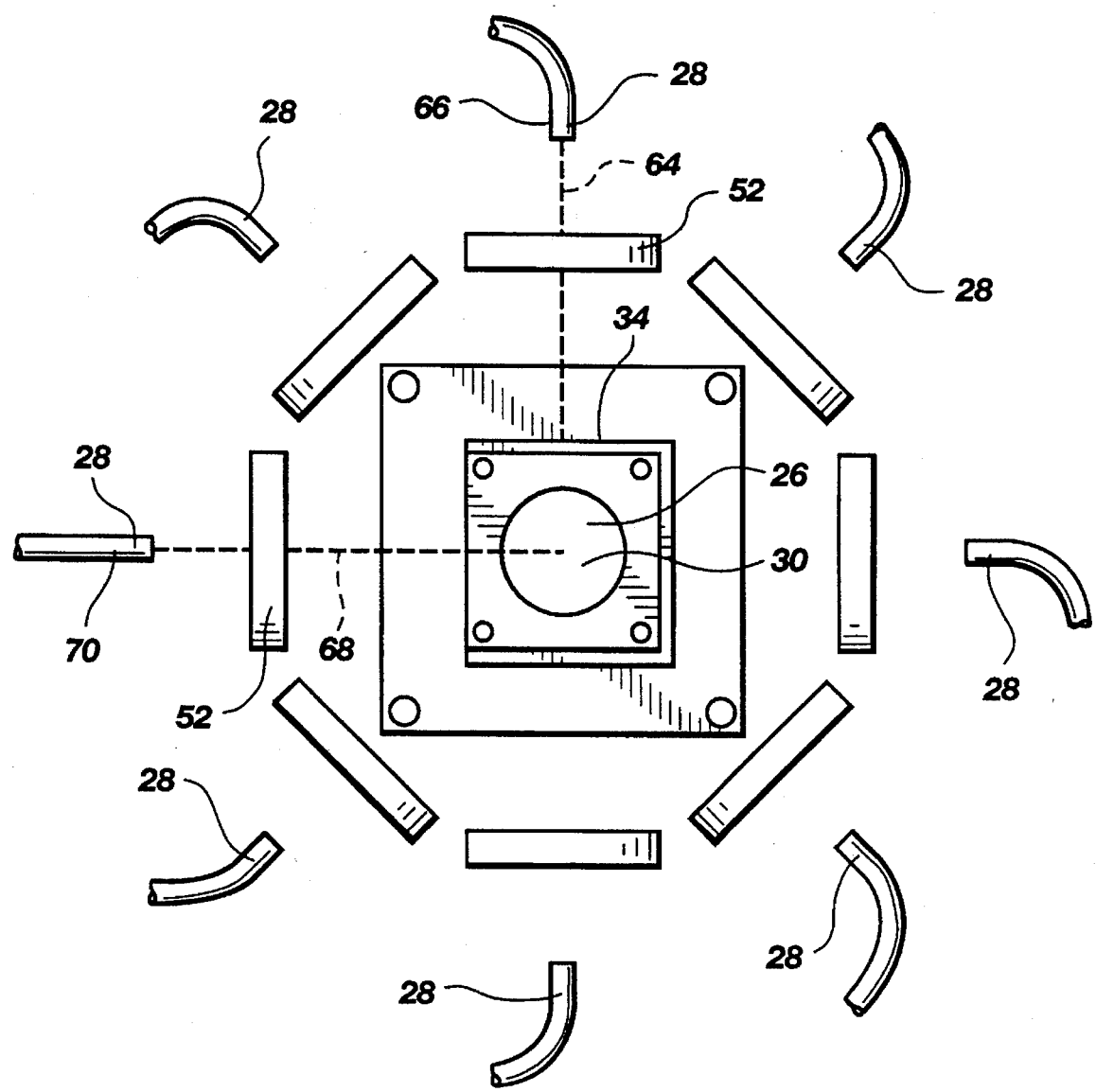
FIG. 4 is a cross-section taken along line 4—4 in FIG. 2.

Alignment of the prism 30 is illustrated in FIGS. 2 and 4. A first light beam 64 is emitted from a first detection emitter 66. The first light beam 64 travels through the corresponding lens 52 toward the prism 30. However, the prism 30 is not aligned with the first emitter 66, so the first light beam 64 does not reach the prism 30. Instead, the first light beam 64 strikes the light barrier 34 and dissipates.

By contrast, a second light beam 68 from a second emitter 70 does reach the prism 30, because the prism 30 has been rotated into alignment with the second emitter 70. Upon reaching the prism 30, the second light beam 68 is directed perpendicular to the plane of FIG. 4, namely, along the central axis 32 toward the light detector 20. After being reflected by the prism 30, the light beam 68 travels through the filter 56 and the baffle 54 to the light detector 20. The light detector 20 then provides the controller 18 (FIG. 1) with a signal corresponding to the intensity of the light beam 68.

With reference to FIGS. 1, 2, and 4, the system 10 does not dedicate one light detector 20 to each well 12 in a row. Instead, the system 10 selectively rotates the prism 30 to align with successively chosen emitters 28. The prism 30 is rotated by the stepping motor 36 as directed by the controller 18. The controller 18 receives a signal from the optical encoder 38 corresponding to the current position of the stepping motor 36 and hence to the current position of the prism 30. It is presently preferred that the prism 30 be rotated to align with each successive emitter 28 in turn (that is, by successive 45 degree clockwise turns in the view of FIG. 4) at the rate of one full revolution per second.

In this manner, the system 10 switches the input from a row of wells 12 toward the single light detector 20 over time. Thus, the present invention substantially reduces the cost and complexity of the light detectors and light detector supporting equipment required to effectively detect light from a row of sample wells 12.

In an alternative embodiment, herein denoted the "fixed prism" embodiment, the reflector includes a removed cone prism fixed in position about a central axis. The removed cone prism assumes the shape swept out by rotating a right-angle prism about the central axis, namely, a cylinder from which a cone is removed. The detection emitters are again stationed in a circle in a plane perpendicular to the central axis, and the light detector is again positioned above the emitter plane on the central axis. A shutter separates each emitter from the removed cone prism. The shutters may be mechanical, but are preferably optical shutters such as polarizers or liquid crystal shutters.

Selectively opening a particular shutter permits the light from the corresponding emitter to be reflected by the prism out of the emitter plane and along the central axis to the light detector. The light from several wells is detected one well at a time by opening the corresponding shutter to allow light from one well to reach the light detector, closing the first shutter and opening a second shutter, and so forth for each well.

A third embodiment is termed the "converging bundle" embodiment. In this embodiment of the system, the reflector includes a fiber optic bundle for each emitter. One end of each bundle is separated from the emitter by a shutter, and the other end of each bundle is positioned near the light detector. The shutters may be mechanical, but are preferably optical shutters such as polarizers or liquid crystal shutters. The detection emitters and the light detector may be stationed in any convenient manner so long as the bundles may carry light from the emitters to the light detector. Thus, selectively opening one shutter permits the light from the corresponding emitter to be carried by the corresponding bundle to the light detector.

In alternative embodiments, excitation shutters, excitation reflectors, and other structures are used to direct light from the excitation light source to selected wells. These excitation structures are in addition to the similar structures used to direct the detection light from the wells to the light detector.

The controller 18 coordinates light detection with liquid handling by communicating with the automated liquid handling system 16. Those of skill in the art may readily determine status and control information which, when directed between the controller 18, the encoder 38, the motor 36, and the liquid handled 16 by known methods, will permit such coordination. Suitable coordination will allow adequate time for the establishment of a base line light measurement to calibrate the system 10, allow adequate time to measure light after compositions are added to the wells 12 or the excitation light 58 is enabled, and otherwise permit effective light detection, light excitation, liquid handling, and sample well positioning.

For clarity of illustration, certain conventional supports and containers are not shown in the drawings. However, those of skill in the art will readily provide suitable mechanical supports for the light detector 20, baffle 54, filter 56, stepping motor 36, lenses 52, emitters 28, and other components of the system 10. In a similar manner, those of skill in the art will readily provide a suitable container for the components illustrated in FIG. 2 to reduce the impact of stray or ambient light upon the light detector 20.

Thus, in a prototype of the system 10, supports included the following: one custom stepping motor stand; one custom sample plate stand; one custom coupler holding the prism 30 to the shaft of the motor 36; eight holders, posts, and stands for lenses, from Newport Corporation of Irvine Calif.; eight holders, posts, and stands for the emitters 28 from Newport Corporation; two holders for dichroic mirror frames, from Newport Corporation; two frames for dichroic mirrors, from the Biomedical Instrumentation Group, University of Pennsylvania, in Philadelphia, Pa.; one eighteen-inch by eighteen-inch optical breadboard from Newport Corporation; one excitation filter holder and stand, from Newport Corporation; and various conventional screws, mounts, bars, and holders.

In summary, the present invention provides a system for detecting light without using a separate light detector for each sample well in a typical row of sample wells. Instead, the light from the first well is carried to the reflector, which reflects the light into the light detector. Next, the second well's emitter is selected, allowing light from the second well to be reflected into the light detector. The third well's emitter is then selected, and the process continues until light from each well in the row has been detected and measured. Unlike conventional approaches, it is not necessary to dedicate one light detector to each well in the row. The liquid handling system then advances the plate, exposing the next row of wells to the light detection system, and the process continues.

The present invention also provides a system which effectively detects fluorescent light having a predetermined wavelength. Filters and a baffle may be employed to remove light outside the desired wavelength range. Collimating lenses may be employed before or after filtering to focus the light for detection by the light detector. Moreover, the present system is readily coordinated with an automated liquid handler so that adequate time is allowed for light detection before the sample plate is advanced.

As described above, one of the significant uses of the apparatus of the present invention is in the screening of drugs and other compounds or reagents for their effects on intracellular free calcium ion concentrations. As mentioned above, for ease of discussion, such materials will be referred to collectively as "drugs." Such drugs may have a wide range of effects on the cell. For example, some drugs are agonists. Agonists are generally defined as compounds which activate a receptor or ion channel. An antagonist, by contrast, is a drug which inhibits or blocks the normal operation or activation of a receptor or ion channel. The fluorescence detection system can be used to screen for both agonist and antagonist drugs, provided that normal activation of the receptor or channel can be measured using fluorescence.

With specific reference to the calcium receptor, a cell surface receptor which is activated by extracellular calcium, drugs which activate the receptor or mimic calcium are referred to as calcimimetic compounds. Drugs which block activation of the calcium receptor are referred to as calcilytic drugs. As will be described later, the fluorescence detection system is used to screen for both calcimimetic and calcilytic drugs.

The screening technique based on the calcium indicators identified above, principally fluo-3, detects changes in intracellular calcium concentration resulting from the activation of the cellular calcium receptor system. The increase in intracellular calcium can be due to the release of calcium from intracellular stores due to activation of the receptor system. Increase in intracellular calcium can also be due to influx of calcium from the extracellular medium directly as a result of the activation of the receptor. Increase in intracellular calcium can be due to influx of calcium from the extracellular medium indirectly through activation of the voltage-dependent calcium channels as a result of depolarization of the membrane potential due to activation of the receptor system.

Using the present invention it is possible to measure changes in calcium ion from any source. The method of the present invention is capable of detecting calcimimetic and calcilytic effects regardless of the receptor, channel, or binding site involved. This is a significant improvement over many conventional testing methods which are site-specific.

It should be recognized that other indicators may also be used in the present invention. Examples of such indicators include Calcium Green-1, Calcium Green-5N, Calcium Orange, Calcium Orange-5N, Calcium Crimson, and Fura Red, all of which are available from Molecular Probes, Eugene, Oreg. Other indicators include fura-2 and indo-1 which are also commercially available.

The methods and apparatus of the present invention allow for sophisticated, high through-put measurement. For example, in vitro assays that measure receptor function, not just binding, are provided for. Assays contain homogenous populations of receptor subtypes, permitting the identification of subtype-selective compounds. Typical cells used in the assay include cells expressing a receptor protein or channel which is capable, upon activation, of directly increasing the intracellular concentration of calcium by opening calcium channels. Alternatively, the cell may indirectly affect the concentration of intracellular calcium by causing initiation of a reaction which utilizes $Ca^{+2}$ as a second messenger (such as G-protein coupled receptors).

Activation of the cellular receptors and ion channels may result in a transient increase in the level of intracellular calcium. The initial increase in calcium may be detected by the fluorescence techniques described herein. These reactions are typically detectable within a few seconds of the addition of the reagent of interest.

A number of known cell lines are usable in order to implement the methods of the present invention. Examples of typical cells of interest include HEK 293 and HuPCaR 4.0 clone #7. HEK 293 cells are well known and readily available human embryonic kidney cells and are described in U.S. Pat. No. 5,024,939. These cells are available from the American Type Culture Collection (ATCC) as accession number CRL 1573. A discussion of the use of these types of cells in calcium channel studies is included in Patent Cooperation Treaty Application No. WO 93/13423 to Akong, et al.

The screening method of the present invention detects any perturbations of normal $Ca^{+2}$ signal transduction by the drug being tested. This screening technique can also be used to develop drugs for any receptor or channel which uses $Ca^{+2}$ as a downstream signal. Other markers for drug action, such as intracellular pH, sodium, or voltage can also be detected in this system if an appropriate fluorescent indicator is used.

With reference to FIG. 1, the procedure used in screening drugs is a straight forward multi-step process. First the wells 16 of the sample plate 14 are loaded with the cell line of interest, such as HEK 293 cells. This typically takes place three to five days prior to running the experiment and the cells are allowed to multiply. This is followed by adding a cell permiant form fluorescence indicator molecule to the test wells 12. As discussed above, several such indicators are presently available. The presently preferred indicator is fluo-3.

Prior to measurement the cells are rinsed with the physiological saline solution.

Following these preparatory steps, the sample plate 14 is positioned on the device 16 and aligned with the row of fiber optic detectors 46. A background signal is measured from a separate row of wells for about 120 seconds. This is followed by the measurement of basal $Ca^{+2}$ for about 20 seconds.

Once these initial procedures are completed, the drug is added to the sample wells 12, while continuously measuring fluorescence with the system 10. This step may be followed by the addition of an agonist which activates the receptor or channel to which the drug will be targeted. At this stage, fluorescence is measured for another period of time at a specific interval following agonist addition. Once the desired measurements have been acquired from a row of sample wells, the multiwell plate is moved to the next row to repeat the procedure described above. At this point a check is made for any effects of the drug on basal $Ca^{+2}$ or on the normal $Ca^{+2}$ signal elicited by the agonist for each well in the plate.

Figure 5:
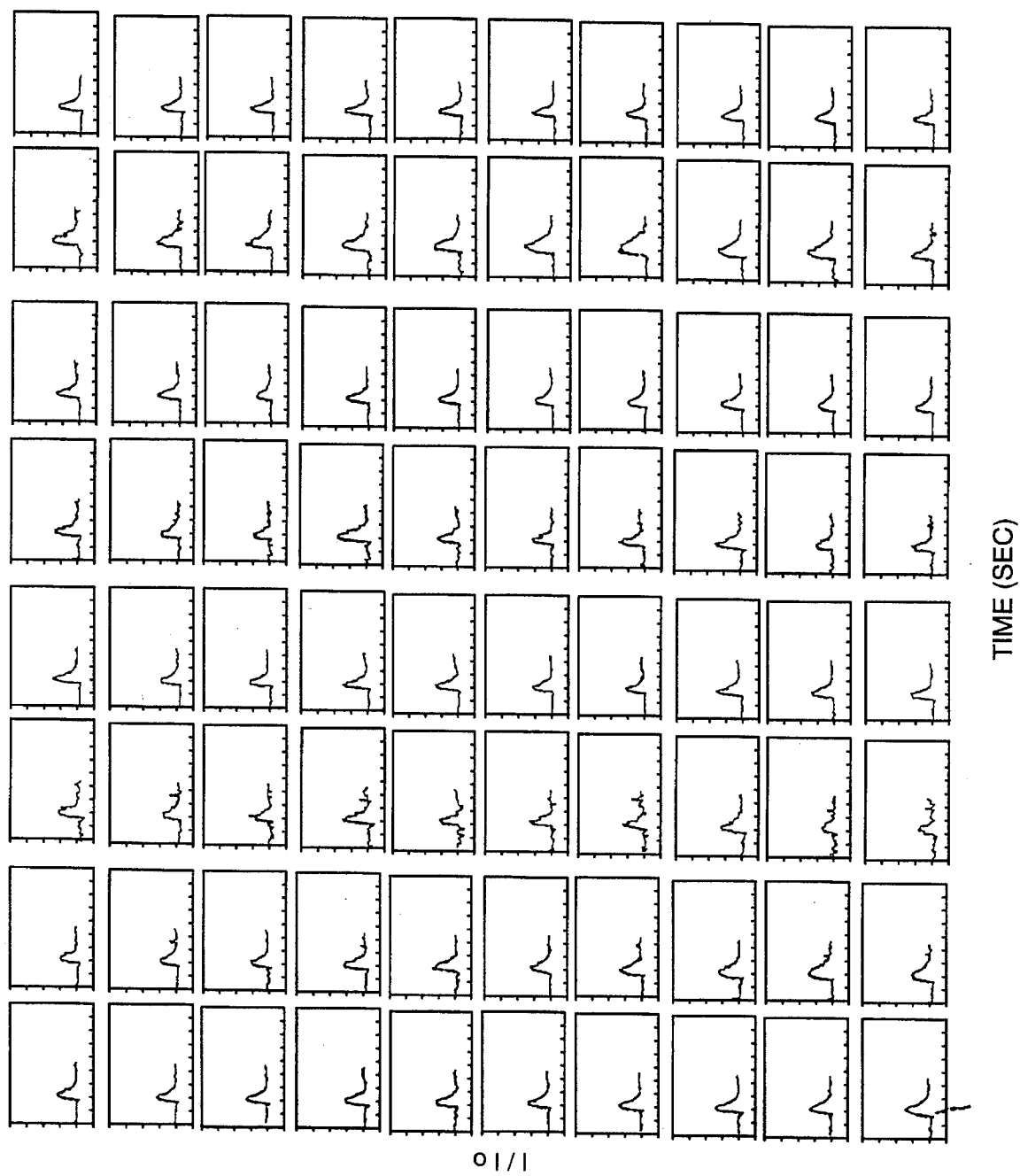
FIG. 5 is representative of the data obtainable using the present invention in connection with a standard 96 well sample plate.

An example of the type of data generated by the method of the present invention is set forth in FIG. 5. The data produced using the fluorescence detection system is quite reproducible. Data from 80 wells in a 96 well plate is shown. HEK-293 cells transfected with the human calcium receptor clone #7 were loaded with fluo-3. The intensity ratio, $I/I_o$, is shown for each well as a function of time. $I/I_o$ is the intensity at the time the measurement was taken divided by the average intensity for the first few points (time zero) before cells are stimulated. Both intensity values I and $I_o$ have the background intensity from a well without cells or a well of cells not loaded with fluo-3 subtracted prior to forming the ratio. Increasing extracellular calcium from 1 to 2 mM in each well elicited an increase in the intracellular free calcium $[Ca^{+2}]$ in the HEK-293 7.0 cells. The increase in calcium as measured by the peak intensity ratio in each well was quite uniform from well to well. The standard deviation of the peak ratio increase divided by the mean peak ratio increase was 9.3% for this experiment.

Figure 6A:
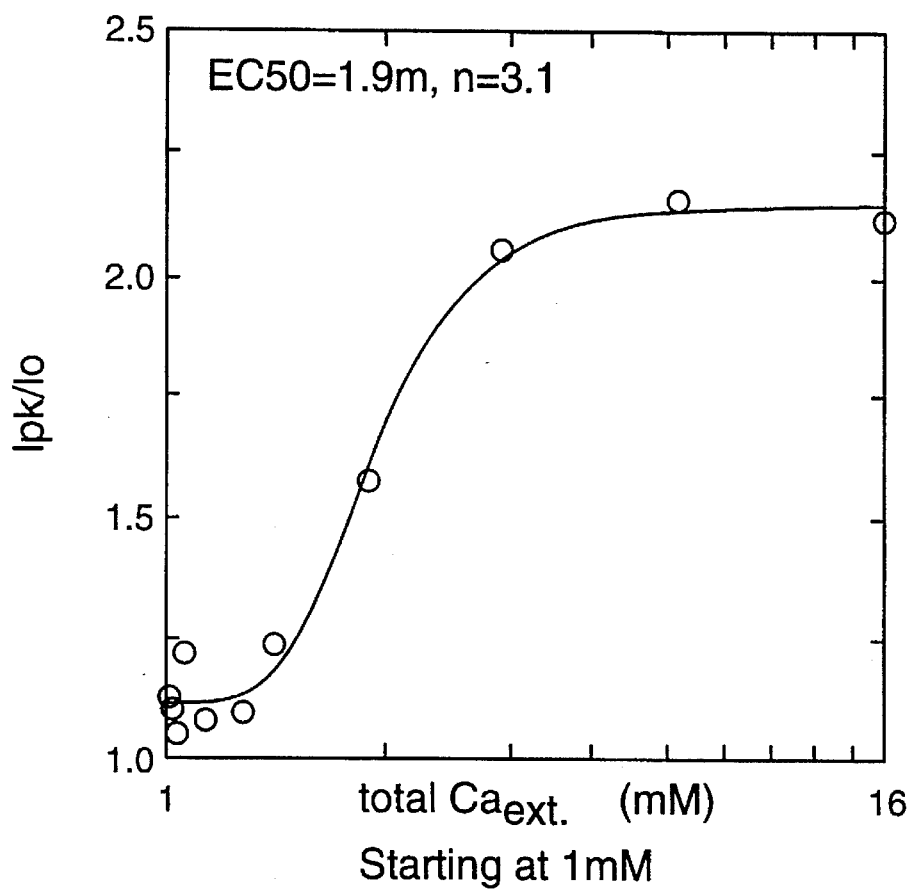
FIGS. 6a and 6b are graphs plotting extracellular calcium ion and are representative dose response curve.
Figure 6B:
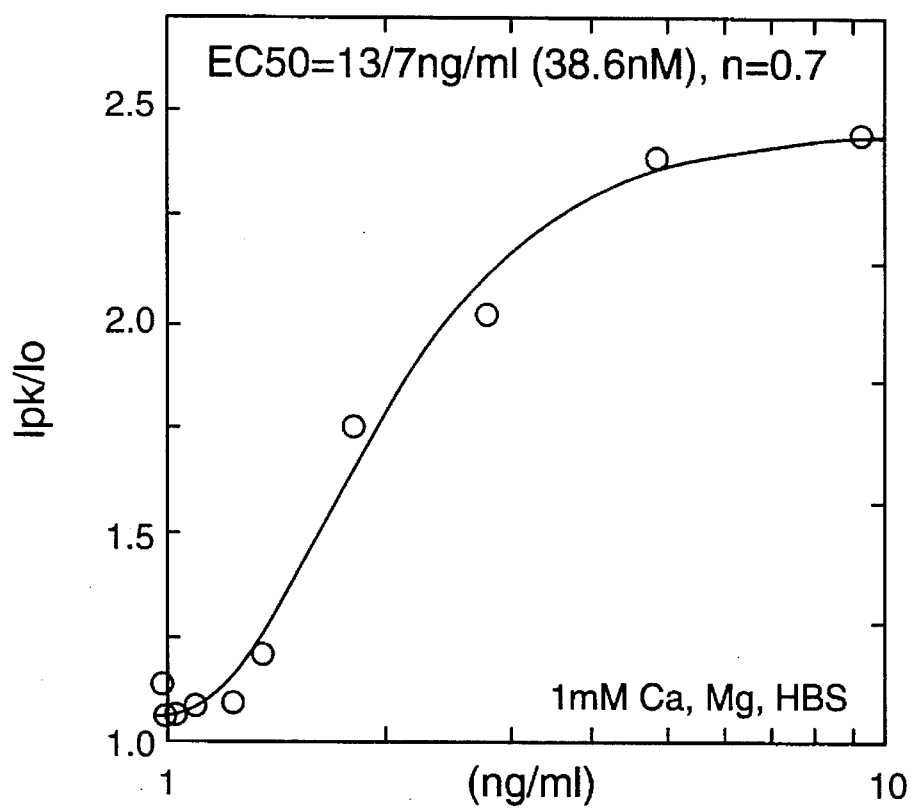

The fluorescence detection system can also be used to characterize drugs as illustrated by FIGS. 6a and 6b. In FIGS. 6a and 6b, dose response curves were produced for both extracellular calcium and a drug, namely NPS 1377 produced by NPS Pharmaceuticals, Salt Lake City, Utah. Data points at different drug or extracellular calcium concentrations represent averages from two adjacent wells of $Ipk/I_o$, the ratio of the peak intensity following stimulation with drug or extracellular calcium divided by the initial intensity in unstimulated cells at the beginning of the experiment. Once again background intensity readings were subtracted prior to forming the ratio.

Figure 7:
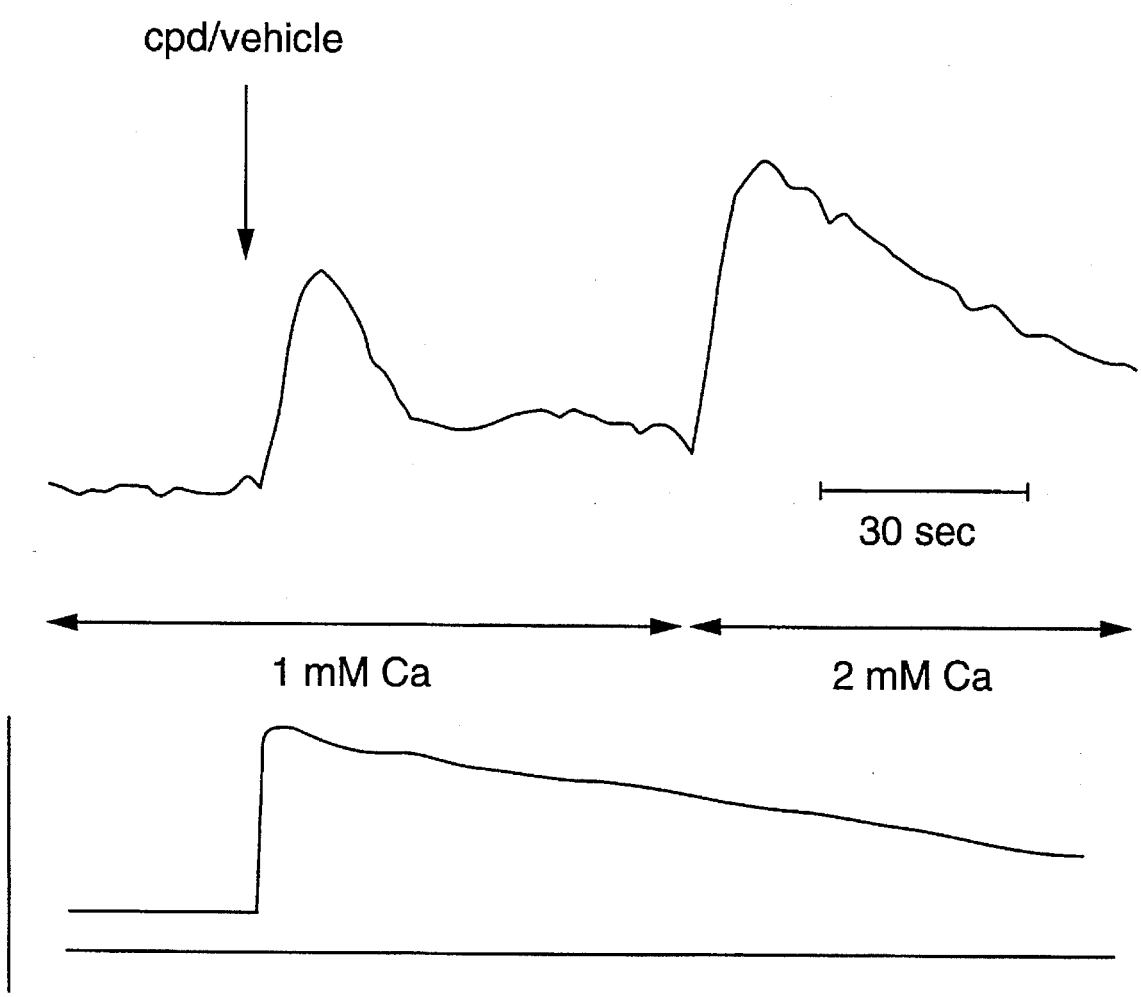
FIG. 7 is a further graph plotting data obtained using the method and apparatus of the present invention.

Data from an example of an actual experiment where compounds were screened for possible drug activity are illustrated in FIG. 7. Sixteen graphs from 16 wells of a 96 well plate are shown in which $I/I_o$, the ratio of intensity divided by the intensity at the beginning of the experiment, is plotted as a function of time. The experimental protocol consists of adding the drug, waiting for about one minute and then increasing extracellular calcium from 1 mM to 2 mM. A decrease or total elimination of the fluorescence normally elicited by increasing extracellular calcium from 1 mM to 2 mM would indicate a potential antagonist to the calcium receptor or calcilytic drug. An increase in intracellular calcium produced by the drug alone prior to increasing extracellular calcium would indicate a possible agonist for the calcium receptor or calcimimetic drug. For each 96 well plate, 16 wells are typically used for control compounds and 8 wells are typically used for background readings.

Thus, the method of the present invention provides an advancement in the art. In one aspect of the method of the present invention, the invention provides rapid screening for both calcimimetic and calcilytic compositions. This method is facilitated by the apparatus of the present invention, and the ability of the apparatus to work in conjunction with the new indicator molecules discussed above.

In summary, the present invention provides a system for detecting light during fluorescence analysis without using a separate light detector for each sample well in a typical row of sample wells. The present invention also provides a system which effectively detects fluorescent light in a predetermined range of wavelengths. The system is used effectively in combination with an automated liquid handler.

The present invention also provides an efficient and effective screening technique for determining the effect that various drugs or other reagents have on calcium function. The screening technique provides screening methods to determine whether a particular drug or reagent is a calcimimetic or calcilytic material.

The invention may be embodied in other specific forms without departing from its spirit or essential characteristics.

The described embodiments are to be considered in all respects only as illustrative and not restrictive. Any explanations provided herein of the scientific principles employed in the present invention are illustrative only. The scope of the invention is, therefore, indicated by the appended claims rather than by the foregoing description. All changes which come within the meaning and range of equivalency of the claims are to be embraced within their scope.

What is claimed and desired to be secured by patent is:

1. An apparatus for detecting light transmitted from a composition disposed in one of a plurality of sample wells, said apparatus comprising:
    a single light detector;
    a reflector comprising means for selectively receiving light from any one of a plurality of detection emitters positioned about said reflector and of reflecting light toward said light detector; and
    a plurality of detection carriers, each of said detection carriers comprising means for carrying light from one of the wells to one of said detection emitters.

2. The apparatus of claim 1, wherein said light detector comprises a photomultiplier tube.

3. The apparatus of claim 1, wherein said reflector comprises a prism.

4. The apparatus of claim 3, wherein said prism is selectively rotatable between a plurality of predetermined positions, said prism having in each position means for receiving light from one of said detection emitters and of reflecting the light toward said light detector.

5. The apparatus of claim 3, wherein said reflector further comprises a plurality of light barriers comprising means for substantially barring said prism from receiving light from more than one of said detection emitters at a time during operation of said apparatus.

6. The apparatus of claim 1, wherein each of said detection carriers comprises a fiber bundle.

7. The apparatus of claim 1, further comprising a plurality of lenses, each of said lenses being positioned between one of said detection emitters and said reflector.

8. The apparatus of claim 1, further comprising:
    an excitation light source; and
    a plurality of excitation carriers, each of said excitation carriers comprising means for carrying light from said excitation light source toward one of the wells.

9. An apparatus for detecting light transmitted from a composition disposed in one of a plurality of sample wells, said apparatus comprising:
    a single photomultiplier tube;
    a prism comprising means for selectively receiving light from any one of a plurality of detection emitters positioned about said prism and of reflecting the light toward said photomultiplier tube; and
    a plurality of detection carriers, each of said detection carriers comprising a fiber bundle comprising means for carrying light from one of the wells to one of said detection emitters.

10. The apparatus of claim 9, wherein said prism is selectively rotatable between a plurality of predetermined positions, said prism in each position comprising means for receiving light from one of said detection emitters and of reflecting the light toward said photomultiplier tube.

11. The apparatus of claim 9, further comprising a plurality of collimating lenses, each of said lenses being positioned between one of said detection emitters and said prism.

12. The apparatus of claim 9, further comprising a wavelength filter positioned between said photomultiplier tube and said prism.

13. The apparatus of claim 12, wherein said wavelength filter comprises a dichroic filter and a bandpass filter.

14. The apparatus of claim 9, further comprising a baffle positioned between said photomultiplier tube and said prism.

15. The apparatus of claim 9, further comprising:
    an excitation light source comprising means for producing excitation light; and
    a plurality of excitation carriers, each of said excitation carriers comprising a fiber bundle comprising means for carrying light from said excitation light source toward one of the wells.

16. The apparatus of claim 15, wherein substantially all of the excitation light produced by said excitation light source has a wavelength lying in a wavelength band about 30 nanometers wide.

17. An apparatus for detecting light in a predetermined wavelength band, the light being transmitted from a composition disposed in one of a plurality of sample wells, said apparatus comprising:
    a single photomultiplier tube;
    a prism comprising means for selectively receiving light from any one of a plurality of detection emitters positioned about said prism and of reflecting the light toward said photomultiplier tube;
    a plurality of collimating lenses, each of said lenses being positioned between one of said detection emitters and said prism;
    a plurality of detection carriers, each of said detection carriers comprising a fiber bundle comprising means for carrying light from one of the wells to one of said detection emitters;
    an excitation light source comprising means for producing excitation light; and
    a plurality of excitation carriers, each of said excitation carriers comprising a fiber bundle comprising means for carrying light from said excitation light source toward one of the wells;
    wherein said prism is selectively rotatable between a plurality of predetermined positions, said prism in each position comprising means for receiving light from one of said detection emitters and of reflecting the light toward said photomultiplier tube.

18. The apparatus of claim 12, wherein substantially all of the excitation light produced by said excitation light source has a wavelength in the range from about 470 nanometers to about 500 nanometers.

19. The apparatus of claim 17, wherein said fiber bundle of one of said detection carriers is interleaved with said fiber bundle of one of said excitation carriers near one of the wells.

20. The apparatus of claim 17, further comprising a wavelength filter positioned between said photomultiplier tube and said prism, said wavelength filter allowing passage of light having a wavelength in the range from about 510 nanometers to about 550 nanometers.

21. The apparatus of claim 17, further comprising a stepping motor having a shaft secured to said prism for selectively rotating said prism between said plurality of predetermined positions.

* * * * *